United States Patent [19]

Dahms et al.

[11] Patent Number: 5,674,475
[45] Date of Patent: Oct. 7, 1997

[54] EMULSIFIER COMPOSITION BASED ON POLYGLYCEROL ESTER

[75] Inventors: Gerd H. Dahms, Velbert, Germany; Masato Tagawa, Tokyo, Japan

[73] Assignees: IFAC GmbH, Germany; Nikko Chemicals Co., Ltd., Japan

[21] Appl. No.: 419,596

[22] Filed: Apr. 7, 1995

[30] Foreign Application Priority Data

Apr. 8, 1994 [DE] Germany .................... 44 12 081.8

[51] Int. Cl.$^6$ .................... A61K 7/42; B01J 13/00
[52] U.S. Cl. .................... 424/59; 252/312; 252/351; 252/356; 514/939
[58] Field of Search .................... 252/312, 351, 252/356; 424/59; 514/938, 939

[56] References Cited

U.S. PATENT DOCUMENTS

| | | | |
|---|---|---|---|
| 3,472,940 | 10/1969 | Osipow et al. | 424/59 |
| 3,695,889 | 10/1972 | Ingerson | 426/602 |
| 3,935,325 | 1/1976 | Gilmore et al. | 426/613 |
| 4,310,561 | 1/1982 | Buddemeyer et al. | 426/601 |
| 4,781,914 | 11/1988 | Deckner | 424/59 |
| 5,039,516 | 8/1991 | Goodman et al. | 424/59 |
| 5,047,232 | 9/1991 | Kaplan | 424/59 |
| 5,143,722 | 9/1992 | Hollenberg et al. | 424/63 |

OTHER PUBLICATIONS

Product Information Bulletin No. 110, C.J. Patterson Company, Kansas City, USA. Date month/year unknown.
Product Information Bulletin No. 125, C.J. Patterson Company, Kansas City, USA. Date month/year unknown.
Drug and Cosmetic Industry, Mar., Apr., May 1969 (reprinted).

*Primary Examiner*—Richard D. Lovering
*Assistant Examiner*—Daniel S. Metzmaier
*Attorney, Agent, or Firm*—Morrison & Foerster LLP

[57] ABSTRACT

Emulsifier composition is a mixture of polyglycerol fatty acid ester ($n \geq 4$) and the lactylate of a fatty acid ($C \geq 8$) or its salt and is used to manufacture a wide range of different O/W emulsions, e.g. sunscreen emulsions for cosmetics. The polyglycerol fatty acid ester preferably has an HLB value $\leq 8$. The emulsifier composition can additionally contain a lipophilic emulsifier.

11 Claims, No Drawings

EMULSIFIER COMPOSITION BASED ON POLYGLYCEROL ESTER

TECHNICAL FIELD

The present invention relates to an emulsifier composition based on polyglycerol fatty acid ester, particularly, the same which is stable against temperature and highly water proof and the emulsion property is little affected by pH. The invention also relates to an O/W emulsion and a sunscreen emulsion or cosmetic manufactured by using such an emulsifier composition.

BACKGROUND OF THE INVENTION

It is known that O/W emulsions or W/O emulsions can be manufactured, in particular for cosmetic purposes, by using emulsifier compositions composed of polyglycerol esters with a degree of polymerization of n<4 and lipophilic emulsifiers.

Lipophilic polyglycerol esters with degrees of polymerization of 4 and above (NIKKO CHEMICAL Co., Ltd., Tokyo/Japan) have not been used for manufacturing O/W emulsions to date. However, they have been used in conjunction with fats, for example, as crystallization-inhibiting agents.

It is known that lactylates—or their alkaline, alkaline earth or ammonium salts (O. J. Patterson Company, Kansas City, USA)—are used to manufacture O/W emulsions and W/O emulsions, especially because these compounds are non-toxic, are permitted under foodstuff legislation, and are biodegradable. For this purpose, the lactylates or their salts are combined with lipophilic emulsifiers such as sorbitan esters, sorbitol esters, glycerol esters, polyglycerol esters such as diglycerol esters, methylglycoside esters, sugar esters, fatty acids and their derivatives, fatty alcohols and their derivatives, and fatty amines and their derivatives.

SUMMARY OF THE DISCLOSURE

Such emulsifier compositions have a serious disadvantage, however, in that they can be employed only within a very narrowly defined pH range and in that their compositions is highly dependent on the pH value. The proportions of lactylate to lipophilic emulsifier by weight must thus be 5:4 at a pH of 5.5, for example, and 1:4 at a pH of 7.5 if the resulting emulsions are to be sufficiently stable (*Product Information Bulletin*, No. 110, C. J. Patterson Company, Kansas City, USA). Furthermore, the proportion is also very dependent on the polarity and concentration of the oil phase in said emulsion; this severely limits the scope of application of said emulsifier composition. Finally the known emulsifier composition is employed at an undesirable high concentration of 5 wt %.

Usually, O/W emulsions are prepared by combining a hydrophilic emulsifier and a lipophilic emulsifier to have a resulting HLB value of 8 to 12. In this case, use of a stabilizer such as wax or polymers is necessary in order to stabilize it at high temperatures under the influence from the phase-inversion temperature. Also there is a tendency for a film applied to skin to be re-emulsified upon contact with water due to the influence of the hydrophilic emulsifier.

On the other hand, W/O emulsions, since they almost do not use hydrophilic emulsifiers, have superior hydrophobic (or water-resistant) property. However, there are a lot of cases that a large amount of wax and oily gelling agent are required in order to make W/O emulsions which are stable at high temperatures, and such W/O emulsions provide an oily feel which are counted as drawbacks.

Accordingly, it is an object of the present invention to provide a novel emulsifier composition which has an improved temperature stability and water-resistant property, and an excellent feel.

It is another object of the present invention to provide an emulsifier composition for the manufacture of stable O/W emulsions that can be used universally to the greatest possible extent, that can be used at comparably low concentrations, and whose effectiveness is virtually independent of the pH of the aqueous phase.

It is a further object of the present invention to provide a stable, water-resistant O/W emulsion and/or cosmetic.

Still further objects of the present invention will become apparent from the entire disclosure.

Surprisingly, it has now been discovered that this object can be attained, in accordance with the present invention, by an emulsifier composition based on polyglycerol (fatty acid) ester, consisting essentially of a mixture of polyglycerol (fatty acid) ester exhibiting a degree of polymerization of $n \geq 4$ and at least one lactylate (derived from a fatty acid) with a carbon number $\geq 8$ or from the salt of said fatty acid.

That is, the emulsifier composition comprises as a lipophilic constituent, a polyglycerol (fatty acid) ester that is not itself effective as an emulsifier, i.e., that has no O/W emulsifying power per se. In actual fact, the emulsifier composition according to the present invention can be used to manufacture a wide rage of O/W emulsions, whereby its function is practically unaffected by the pH of the aqueous phase.

The present invention provides also an O/W emulsion comprising said emulsifying composition as an emulsifying component in the oil phase.

The resulting emulsions have superior stability and feeling upon application and have an excellent hydrophobic (i.e., water-resistant) property of the resultant film. The invented emulsifier composition can provide stable O/W emulsions generally at a low concentration, i.e., ranging from 1 to 4% by weight, preferably from 1.5 to 3.5% by weight, without being adversely affected by the components of O/W phases.

As mentioned earlier, the lactylates used in the composition are non-toxic and biologically degradable, and thus the resulting emulsifier composition has the same advantages, too.

The present invention provides a sunscreen cosmetic comprising the abovementioned emulsifier composition and at least one UV ray absorbing agent, generally of organic nature and/or inorganic micropigments having UV ray screen effect. This sunscreen cosmetic has excellent water-resistant (or waterproof) property and UV ray screening effect, and any kind of skin care agent can be added to it.

The concentration of the emulsifier composition according to the present invention is largely independent of the components of the oil phase and the water phase and can be generally in the range between 1 and 4 wt %, preferably between 1.5 and 3.5 wt %.

The emulsions manufactured with said emulsifier composition according to the present invention exhibit storage and temperature stability (at least 8 weeks at 40° C. and 4 weeks at 50° C.; 10 thaw-freeze cycles at −18° C./+40° C. In addition, they are demonstrably water-resistant (or waterproof); following application to a surface and a drying period of 30 minutes, a homogeneous oil film is formed which cannot be redispersed in water.

PREFERRED EMBODIMENTS

The advantageous compositions of the emulsifier composition according to the present invention, as well as of the sunscreen emulsions (cosmetics) manufactured with said emulsifier composition, are characterized in additional claims. In particular, the proportions of polyglycerol fatty acid ester to lactylate (and/or its salt) by weight can be chosen within a wide range of 20:1 to 1:20. This range can be established independent of the pH of the aqueous phase. Below 1:20, it results in unstable tendency against temperature and lowering in water-resistant property. Above 20:1 O/W emulsions are difficult to be produced.

The polyglycerol fatty acid ester preferably has an HLB value≦8. Preferably the fatty acid of the lactylate has been chosen from the group of saturated, unsaturated branched and/or hydrophilic substituted fatty acids. The emulsifier composition can additionally contain a lipophilic emulsifier. The lipophilic emulsifier may be chosen from sorbitan fatty acid esters, sorbitol fatty acid esters, propylene glycol fatty acid esters, glycerol fatty acid esters, polyglycerol fatty acid such as diglycerol fatty acid esters, methylglycoside fatty acid esters, alkyl polyglycoside, sugar fatty acid esters fatty acids and their derivatives, fatty alcohols and their derivatives, fatty amines and their derivatives, or a mixture of these.

An ester having a polymerization degree n or 4 or more is used as the ester of polyglycerol and fatty acid. Esters outside this range are poor in lipophilic property, emulsifying power and water-resistance. It is preferred to use esters with fatty acids having 12 or more carbon numbers. As for the HLB, 8 or less is preferred for the polyglycerol fatty acid ester, since an HLB exceeding 8 will bring about lowering the water-resistance. Also, a solid one is preferred, since a liquid one will bring about lowering the stability at high temperatures.

As for the polyglycerol fatty acid esters, the following esters are enumerated; tetraglyceryl (di, tri, or tetra)-laurate, -myristate, -palmitate, -stearate, or -behenate, hexaglyceryl (di, tri, tetra, or penta) -laurate, -myristate, -palmitate, -stearate, or behenate; decaglyceryl (tri, tetra, penta, hepta, or octa) -laurate, -myristate, -palmitate, -stearate or -behenate etc.

The lactylate (or salt thereof) used in the present invention has a carbon number preferably of 8 or more. With a carbon number less than 8, an inferior emulsifying property results. The fatty acids from which the lactylate is derived comprise one or more selected from the group of saturated, unsaturated and branched fatty acids, and those having substituted hydrophilic groups. The salt of lactylate may be salts of alkali metal (e.g., Na, K etc), alkaline earth, ammonium and triethanol amine, or the like.

Such lactylates (or salt thereof) may include, caproyl lactate and its salts of a class of Na, Ca, Mg, ammonium, triethanol amine; 2-ethylhexanoyl lactate, lauroyl lactate, myristoyl lactate, palmitoyl lactate, stearoyl lactate, isostearoyl lactate, oreoyle lactate, 12-hydroxystearoyl lactate, lysinoreyl lactate, etc. and those salts of the same class.

The emulsifier composition may further comprise a higher alcohol and/or a lipophilic emulsifier. The higher alcohol may comprise, for instance, myrityl alcohol, cetyl alcohol, stearyl alcohol, behenyl alcohol, etc. The lipophilic emulsifier comprises, for instance, sorbitan fatty acid esters, glycerol fatty acid esters, polyglycerol fatty acid esters, methylglycoside fatty acid esters, sugar fatty acid esters, fatty acids and their derivatives, fatty alcohols and their derivatives, fatty amines and their derivatives, or a mixture of those.

The fatty alcohol derivatives comprise amphiphilic and swellable solid substances, e.g., polyoxyethylene (2) cetyl ethers or polyoxyethylene (3) stearyl ether. The fatty acid amines include stearic acid mono-ethanol amide, polyoxyethylene (2) stearyl amine etc. The fatty acid derivatives include propylene glycol monostearate, diethylene glycol distearate etc.

Such additional components may be present, preferably in an amount of 50% by weight or less of the entire emulsifier composition. Exceeding 50% by weight, the oily feeling (stickiness) is enhanced and unfavorable. It is preferred to maintain the amount of those additional components in an amount of at least 2% by weight in the entire emulsion. In other words, it is preferred that the invented emulsifier composition comprises the polyglycerol fatty acid ester and lactylate (and its salts) in an amount of at least 50% by weight of the entire composition.

The amount of the emulsifier composition in the entire emulsion should be preferably about 1 to 4 % by weight of the entire emulsion, more preferably 1.5 to 3.5% by weight. Below 1% by weight, the resultant emulsion has inferior stability than the case above this amount, although the emulsifying property is observed. On the other hand, its presence exceeding 4% by weight does not further improve the emulsifying effect, counted as uneconomical.

The present invention provides a sunscreen cosmetic or O/W emulsion which contains a sunscreen agent and has excellent waterproofness. The sunscreen agent is preferably present in an amount of 0.1 to 10% by weight in the entire cosmetic.

It is further preferred for the sunscreen cosmetic to include a skin care agent. The skin care agent may be present either in the oil phase or aqueous phase, and may be those which are generally used in cosmetics as emollient agent, whitening agent, astringent agent, skin nutrient and the like. Concretely, the skin care agent includes glycerin, saccharides, glycols, vitamins and their derivatives, extracts from animals or vegetables, amino acids and derivatives of the same, mucopolysaccharides, organic acid and salts thereof etc. Therefore, any desired cosmetic effect can be afforded. It is not excluded for the invented cosmetics to further include other ingredients which are generally used in the cosmetics such as perfumes, pigments, preservatives, thickeners, etc.

The sunscreen emulsifier may be prepared by comprising the emulsifier as mentioned hereinabove, and further comprising a sun-screen agent which may be chosen from organic sunscreen agents and inorganic sunscreen micronized pigments and a skin care agent.

The present invention will be described in the following on the basis of several examples.

EXAMPLES

Example 1

This example illustrates in general the composition of the emulsifier and the manufacture of an O/W emulsion with said emulsifier.

An emulsifier consisting of hexaglycerol pentasteartate (2.2 parts by weight) and sodium stearoyl lactylate (0.3 parts by weight) is added to an oil phase consisting of 5 parts by weight of sunflower oil, olive oil and avocado oil, respectively.

An aqueous phase (77.25 parts by weight) contains glycerol (4 parts by weight), 5-ureidohydantoin (allantoin: 0.2 parts by weight), panthenol (0.8 parts by weight) and xanthan gum (0.25 parts by weight).

The oil phase and the aqueous phase are each heated separately to a mixing temperature in the 60 ° C. to 90° C. range, preferably to 80° C.; while being stirred with a normal mixer, the two phases are combined and homogenized (1 minute at 80° C.) The O/W emulsion obtained in this manner is cooled to 25° C. in a water bath, while being stirred gently. Finally, a preservative (Phenonip: 0.2 parts by weight) is added while the emulsion is continuously stirred gently.

The O/W emulsion manufactured in this manner has the properties described in the foregoing.

Example 2

This example and the following examples additionally contain a lipophilic emulsifier, e.g., higher alcohol.

An emulsifier consisting of decaglycerol pentastearate (1.435 parts by weight) and sodium stearoyl lactylate (0.315 parts by weight) are added to the oil phase consisting of 10 parts by weight of paraffin oil; in addition, a lipophilic emulsifier (behenyl alcohol; 1.75 parts by weight) is also added.

An aqueous phase consists of demineralized (ion-exchanged) water (86.3 parts by weight).

Following the manufacture of the O/W emulsion as in Example 1 and the addition of the preservative (Phenonip: 0.2 parts by weight), an O/W emulsion with the same properties described in the foregoing is obtained.

EXAMPLE 3

This example is intended to show that the polarity of oil phase has no effect on the effectiveness of the emulsifier; in this context, the composition corresponds to that shown in claim 1.

An emulsifier consisting of 1.435 parts by weight of decaglycerol pentastearate and 0.315 parts by weight of sodium stearoyl lactylate and the same amount of the lipophilic emulsifier sorbitan monostearate (1.75 parts by weight) are added to the oil phase consisting of Caprin (glycerol tricaprylate, 10 parts by weight).

As in Example 2, the aqueous phase consists of demineralized water (86.3 parts by weight).

As in Example 2, the aqueous phase consists of demineralized water (86.3 parts by weight).

An O/W emulsion is manufactured as in Example 1. Despite the significantly increased polarity of the oil phase at the same emulsifier concentration, the O/W emulsion obtained has the same properties as that of Example 1.

The following examples are intended to show a practical application, using a sunscreen emulsion as an example; it has been ascertained in this context, moreover, that the various additives do not have any impact on the effectiveness of the emulsifier.

EXAMPLE 4

A sunscreen emulsion in which the sunscreen agent is contained in the aqueous phase has the following composition:

The oil phase contains an emulsifier (1.33 parts by weight of decaglycerol pentastearate, 0.92 parts by weight of sodium stearoyl lactylate), a lipophilic emulsifier (1.75 parts by weight of behenyl alcohol); and a mixture containing equal parts of paraffin oil (7.5 parts by weight) and Caprin (7.5 parts by weight).

The aqueous phase contains glycerol (4.0 parts by weight), 5-ureidohydantoin (allantoin: 0.2 parts by weight), panthenol (0.8 by weight), a sunscreen (UV-absorbing) agent (2-phenylbenzimidazol 5-sulfonic acid; 3 parts by weight), xanthan gum (0.25 parts by weight) and demineralized water (72.55 parts by weight).

Following the manufacture of the O/W emulsion as in Example 1 and the addition of the same preservative (Phenonip; 0.2 parts by weight), an O/W emulsion is obtained which, despite its altered composition, has the same properties as the emulsion according to Example 1.

EXAMPLE 5

A sunscreen emulsion, in which the sunscreen agent is contained in the oil phase, has the following composition:

The oil phase contains, in significantly reduced amounts, an emulsifier of the same kind as before (0.57 parts by weight of decaglycerol pentastearate; 0.18 parts by weight of sodium stearoyl lactylate, and 0.75 parts by weight of behenyl alcohol), a sunscreen agent (8.0 parts by weight of octyl methoxycinnamate, 5.0 parts by weight of isoamyl-p methoxycinnamate), and Caprin (5.0 parts by weight).

The aqueous phase contains glycerol (4.0 parts by weight), 5-ureidohydantoin (allantoin 0.2 parts by weight and panthenol (0.8 parts by weight) and, in addition, polyacrylic acid (neutral; 0.2 parts by weight), magnesium aluminum silicate (0.2 parts by weight), and demineralized water (74.9 parts by weight.

Following manufacture of the O/W emulsion as in Example 1 and the addition of the same preservative (Phenonip; 0.2 parts by weight), an O/W emulsion is obtained which has the same properties as the emulsion in accordance with Example 1, despite an altered composition and a significantly reduced emulsifier concentration.

Example 6

A sunscreen emulsion containing an inorganic pigment serving as a sunscreen agent in the oil phase and having the following composition:

The oil phase contains an emulsifier (1.33 parts by weight of decaglycerol pentastearate; 0.42 parts by weight of sodium stearoyl lactylate; 1.75 parts by weight of behenyl alcohol) and, in addition, 0.5 parts by weight of decaglycerol pentaisostearate 15.0 parts by weight of a sunscreen agent (Tioveil OP; a micronized titanium dioxide dispersion (40% in octyl palmitate)); and equal parts (each 3.0 parts by weight) of paraffin oil and Caprin.

The aqueous phase contains glycerol (4.0 parts by weight), 5-ureidohydantoin (allantoin; 0.2 parts by weight), panthenol (0.8 parts by weight), xanthan gum (0.25 parts by weight) and demineralized water (69.55 parts by weight).

Following manufacture of the O/W emulsion as in Example 1 and the addition of the same preservative (Phenonip; 0.2 parts by weight), an O/W emulsion is obtained which has the same properties as the emulsion in accordance with Example 1, despite an altered composition.

In comparison with commercial sunscreen emulsions, the sunscreen emulsions described in the above Examples 4 to 6 exhibit higher SPF, the sun protection factor, which are determined in the usual manner. They are distinguished from the commercial sunscreen emulsions by their significantly improved waterproofness.

During the investigation of the effect of pH on the emulsion manufactured in accordance with the above examples, it was found that reducing the pH from 7.5 to 4.5) citric acid buffer) did not alter the properties of the emulsions.

The O/W emulsions may also contain other lipophilic emulsifiers instead of behenyl alcohol; for the purpose of expediency, these should be selected from the group of fatty acid esters such as sorbitan esters, glycerol esters, polyglycerol esters, methylglycoside esters, sugar esters; fatty acids and their derivatives; fatty alcohol derivatives; fatty amines and their derivatives; or a mixture of same. In this context, the solid amphiphilic, swellable substances may be present in the form of fatty alcohol derivatives, e.g., as polyoxyethylene (2) cetyl ethers or as polyoxyethylene (3) stearyl ethers; the fatty amine derivatives may be present, for example, as stearic acid mono-ethanol amide or polyoxyethylene (2) stearyl amine, and the fatty acid derivatives, for example, as propylene glycol monostearate or diethylene glycol distearate.

As exemplified above, the emulsifier composition according to the present invention can provide O/W emulsions with excellent temperature stability and water-resistancy. It is non-toxic, safe for human due to the use of lactylate and salts of same which are bio-degradable. Furthermore, the emulsifying property is little affected by pH and composition, and emulsions can be prepared using the specific small amount, and thus it is very useful and applicable in a wide range of fields.

The O/W emulsions of the present invention have excellent temperature stability and water-resistancy: an oil film obtained after application followed by drying cannot be reemulsified. Furthermore, the O/W emulsions have a lower content of the emulsifier composition, and thus can exhibit excellent feel and low irritation and can effectively contain other active ingredients.

The film sunscreen cosmetics of the present invention does not reemulsify upon contact with water. The film has excellent water-resistancy so it resists degradation through perspiration and has excellent sun-screening effect. It can contain any desired skin care agents offering significant advantage to afford cosmetic effect.

It should be noted that the present invention is not limited to those embodiments herein disclosed but allow modifications which can be made based on the generic concept or gist and scope of the present invention as disclosed herein and as defined in the following claims.

What is claimed is:

1. An emulsifier composition based on polyglycerol fatty acid ester, consisting essentially of:

polyglycerol fatty acid ester having a polymerization degree n of at least 4 and an HLB value of 8 or less, at least one lactylate or salt thereof derived from a saturated non-branched fatty acid with a carbon number of at least 8, and a lipophilic emulsifier which is a higher alcohol having a carbon number of 14 to 22 wherein said polyglycerol and said lactylate are present in a proportion of polyglycerol to lactylate by weight in the range between 1:20 and 20:1.

2. An emulsifier composition as defined in claim 1 wherein said saturated non-branched fatty acid has a carbon number of 22 or less, and said polyglycerol fatty acid ester has an average polymerization degree n of 10 or less.

3. An emulsifier composition as defined in claim 1 wherein the fatty acid of the lactylate is has a carbon number of 8 to 18.

4. The emulsifier composition of claim 3 wherein the fatty acid of the lactylate is 12-hydroxystearic acid.

5. An emulsifier composition as defined in claim 1, wherein said higher alcohol is selected from the group consisting of mirystyl alcohol, cetyl alcohol, stearyl alcohol and behenyl alcohol.

6. An emulsifier composition as defined in claim 4, wherein the fatty acid of said polyglycerol fatty acid ester has a carbon number of 12 or more.

7. A sunscreen cosmetic comprising the emulsifier as defined in claim 1, and at least one sunscreen agent selected from the group consisting of organic UV absorbing agents and inorganic sunscreen micropigments.

8. A sunscreen cosmetic comprising the emulsifier as defined in claim 1, and at least one sunscreen agent selected from the group consisting of organic UV absorbing agents and inorganic sunscreen micropigments, and further contains a skin care agent.

9. An O/W emulsion comprising the emulsifier compositions as defined in claim 1 in its oil phase.

10. An O/W emulsion as defined in claim 9, wherein said emulsifier composition is present in an amount of 1.0 to 4.0 percent by weight of the entire O/W emulsion.

11. An O/W emulsion as defined in claim 9, wherein said emulsifier composition is present in an amount of 1.5 to 3.5 percent by weight of the entire O/W emulsion.

* * * * *